(12) United States Patent
Pearson

(10) Patent No.: US 9,375,540 B2
(45) Date of Patent: Jun. 28, 2016

(54) NASAL AROMA BREATHING PIPE

(76) Inventor: Scott Pearson, Amberley (NZ)

(*) Notice: Subject to any disclaimer, the term of this patent is extended or adjusted under 35 U.S.C. 154(b) by 199 days.

(21) Appl. No.: 14/123,481

(22) PCT Filed: Jun. 7, 2012

(86) PCT No.: PCT/NZ2012/000086
§ 371 (c)(1),
(2), (4) Date: Dec. 2, 2013

(87) PCT Pub. No.: WO2012/169905
PCT Pub. Date: Dec. 13, 2012

(65) Prior Publication Data
US 2014/0096767 A1    Apr. 10, 2014

(30) Foreign Application Priority Data
Jun. 7, 2011   (NZ) .......................... 593272

(51) Int. Cl.
*A61M 15/06*   (2006.01)
*A61M 15/00*   (2006.01)
*A61M 21/00*   (2006.01)
*A61M 16/10*   (2006.01)

(52) U.S. Cl.
CPC ........... *A61M 15/06* (2013.01); *A61M 15/0091* (2013.01); *A61M 16/107* (2014.02); *A61M 21/00* (2013.01); *A61M 2021/0016* (2013.01)

(58) Field of Classification Search
CPC .......... A61M 15/0091; A61M 16/107; A61M 15/06; A61M 15/08; A61M 11/08
USPC ..................................................... 128/202.21
See application file for complete search history.

(56) References Cited

U.S. PATENT DOCUMENTS 3,410,273 A * 11/1968 Bolles ........................... 131/271
3,695,275 A * 10/1972 Hayward ...................... 131/271
5,308,314 A *  5/1994 Fukui et al. .................. 604/6.11

* cited by examiner

*Primary Examiner* — Kristen Matter

(57) ABSTRACT

The claimed invention is an apparatus to assist and encourage a person to take long, deep and steady breaths. The invention is designed to provide improved health for the user by fostering; improved breathing and relaxation, aroma delivery and positive smell association, calmer clearer thinking, reduced stress and anxiety, as well as providing a substitute for potentially harmful habits such as smoking, over-eating, over-drinking and other forms of drug abuse. This invention may also reduce the impact of some existing physiological and psychological health conditions.

2 Claims, 4 Drawing Sheets

SECTION A-A

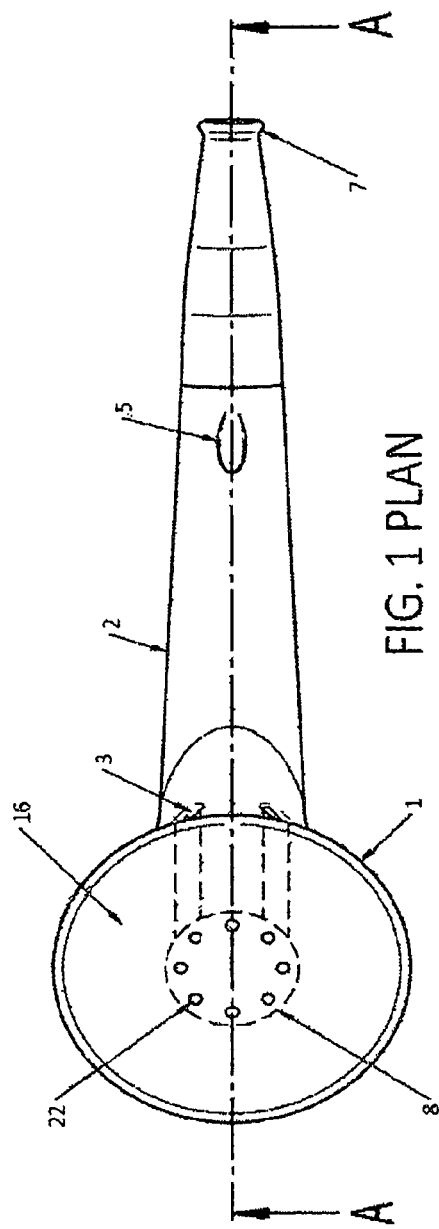
FIG. 1 PLAN

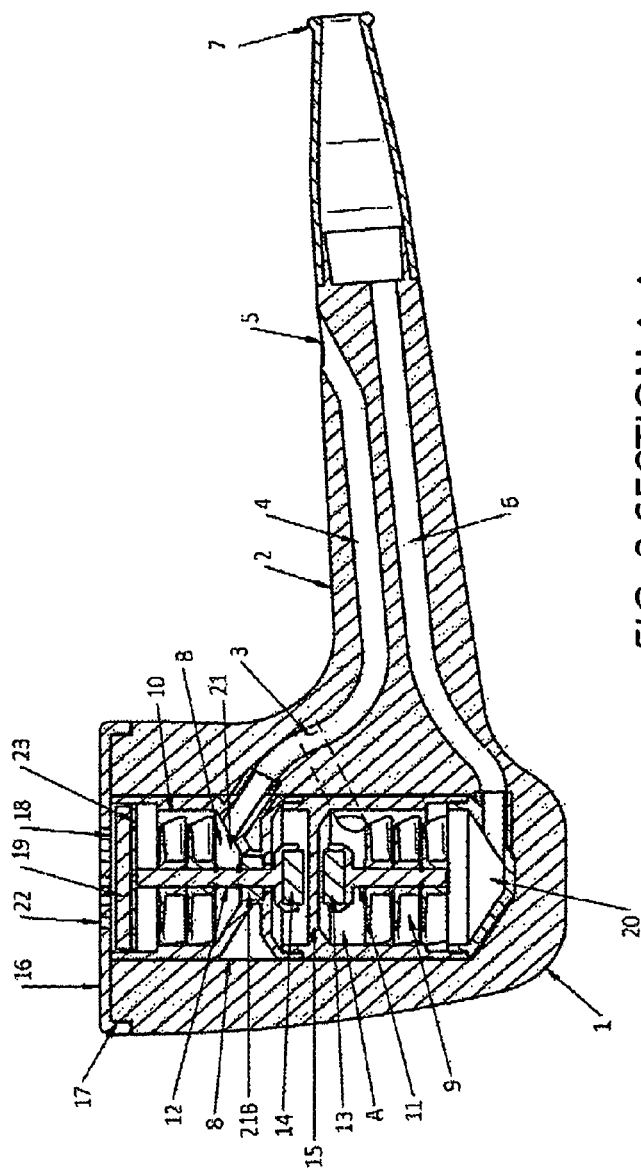
FIG. 2 SECTION A-A

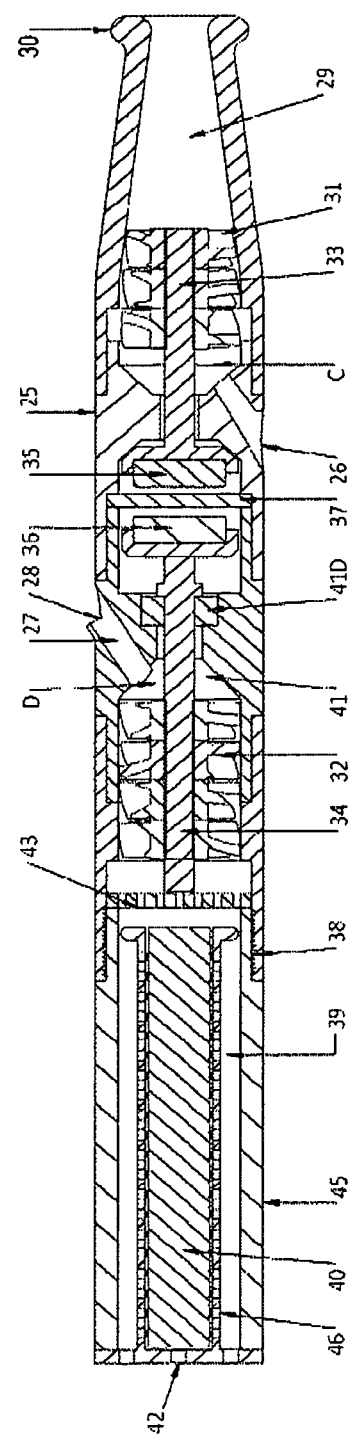
FIG. 3 SECTION

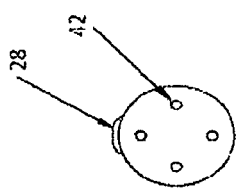
FIG. 4 END ELEVATION

NASAL AROMA BREATHING PIPE

CROSS-REFERENCE TO RELATED APPLICATIONS

Not Applicable

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable.

STATEMENT REGARDING PRIOR DISCLOSURES BY THE INVENTOR OR A JOINT INVENTOR

Not Applicable.

BACKGROUND OF THE INVENTION

1) Field of the Invention

The invention relates to a breathing and aroma delivery apparatus.

2) Description of Related Art Including Information Disclosed Under 37 CFR 1.97 and 1.98

| U.S. Patent Documents Cited | | |
|---|---|---|
| U.S. Pat. No. 3,410,273 | November 1968 | Chadbourn Bolles James |
| U.S. Pat. No. 5,308,314 | May 1994 | Fukui et al. |
| U.S. Pat. No. 3,695,275 | October 1972 | Hayward, Leonard |
| WO/2001/023024 PCT/US2000/026565 | September 2000 | Davi, Richard. A |
| U.S. Pat. No. 2,996,066 A | December 1960 | Marquette Edmond RT |

| Foreign Patent Documents Cited | | | |
|---|---|---|---|
| WO/2009/134164 | April 2009 | Russia | URTSEV,Vladimir Nikolaevich KHABIBULIN, Dim Maratovich |
| WO/2007/131449 | May 2007 | CHINA | HAN, Li |

BRIEF SUMMARY OF THE INVENTION

The present invention is directed to a device to assist and encourage a person to take long, deep and steady breaths. The invention is designed to provide improved health for the user by fostering; improved breathing and relaxation, positive smell association, calmer clearer thinking, reduced stress and anxiety, as well as providing a substitute for potentially harmful habits such as smoking, over-eating, over-drinking and other forms of drug abuse. This invention may also reduce the impact of some existing physiological and psychological health conditions.

The invention is designed to provide benefits for a wide range of people and may reduce negative health effects, including provision of an alternative substitute for potentially harmful behaviors or habits. The device can also improve the health and well-being of the user through providing an enjoyable breathing and aromatherapy experience that can initiate a mental "time-out" break for the user. The said device can therefore assist; those affected by stress and anxiety whether mild or severe; those with negative eating, drinking or drug-taking habits; or those who would enjoy or benefit from the physical and emotional advantages of using the said device.

Some of these potential benefits can be derived from other 'prior art' such as; aroma delivery devices like WO/2001/023024, as well as electronic and smokeless cigarettes or pipes such as WO/2009/134164 and WO2007/131449. Most of the prior art electronic cigarettes simulate the activity of smoking.

The prior art electronic cigarette devices disturb people sitting next to the user by smelling and seeing the scented smoke-like air either directly from the device or in a secondary fashion after exhalation by the user. Thus the prior art devices are not suitable for use in public spaces such as cinemas, concert halls and planes where the user may wish to avoid spreading the aroma and visible gases onto others in their vicinity. 'Prior art' such as electronic cigarettes and smokeless cigarettes and pipes, lead to a significant volume of 'passive' scented or chemically altered air being exhaled by the user after breathing this altered air directly into and then out of the lungs in significant volumes.

It is an object of the present invention to address the foregoing problems.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

Further aspects and advantages of the present invention will become apparent from the ensuing description which is given by way of example only.

BRIEF DESCRIPTION OF THE SEVERAL VIEWS OF THE DRAWINGS

Further aspects of the present invention will become apparent from the ensuing description which is given byway of example only and with reference to the accompanying drawings in which:

FIG. 1 Plan view of the apparatus for a Bowl Pipe configuration;

FIG. 2 Section A-A view of the apparatus for a Bowl Pipe configuration;

FIG. 3 Section view of the apparatus for a Cylinder Pipe configuration; and

FIG. 4 End elevation view of the apparatus for a Cylinder Pipe configuration;

BRIEF SUMMARY OF THE INVENTION

According to one aspect of the present invention there is provided a breathing and aroma delivery apparatus comprising of:
- a first, second and third cylindrical compartment;
- wherein the said first compartment comprises;
- a mouthpiece, said mouthpiece being attached to the first compartment and forming an air outlet adapted for allowing a user to draw air through an end of the mouthpiece; and
- a driving link located between the first and second compartments, the driving link creating a mechanical coupling between the first and second compartments;
- wherein the driving link is separated by a partition that prevents mixing of gases between the first and second compartments;
- wherein said first compartment comprises:
- an air extractor, said air extractor comprising of a center axle with fan blades that extend in a perpendicular direction from the center axle, the center axle extending in a longitudinal direction within the first compartment;
- a funnel and an external air channel, said funnel and said external air channel concentrating ambient air when propelled from the air extractor through the mouthpiece and the air outlet; and
- one or more air inward ventilation holes located upstream of the air extractor and in communication with atmosphere;
- wherein said second compartment comprises:
- an active substance extractor, said active substance extractor extracting an active substance transported by air, said active substance extractor comprising a center axle with fan blades extending in a perpendicular direction from the center axle, the center axle extending in a longitudinal direction within the second compartment;
- a funnel, an external air channel, and an outlet nozzle, said funnel, said external air channel, and said outlet nozzle concentrating and propelling the active substance from the active substance extractor to outside of the device, the outlet nozzle being adapted to direct the active substance towards a user's nostrils;
- wherein said third compartment comprises:
- a holder for holding the active substance, the active substance capable of being transported by air and becoming volatile when exposed to the atmosphere;
- inward ventilating holes, said inward ventilating holes being upstream of the active substance and connecting the third compartment with the atmosphere to allow air to be drawn into the third compartment and over the active substance; and
- a permeable membrane, said membrane allowing the active substance to be drawn from the third compartment and into the second compartment; and
- wherein when the user inhales through the mouthpiece, the air extractor rotates, causing the active substance extractor to rotate via the driving link, which propels active substance into the user's nostrils while the user inhales ambient air through the air outlet of the mouthpiece.

The term compartment is understood to be a section of an apparatus, device or means.

For the purpose of the invention, the compartment is understood to be a section of the breathing and aroma delivery apparatus, with arrangements of different parts within each section.

The term mouthpiece is a part or device to which the mouth is applied.

For the purpose of the invention, the mouthpiece is a part or device of which a user of the breathing apparatus can apply his/her mouth to in order to suck or blow to create a fluid flow within the apparatus. The size of the mouthpiece and its aperture can be altered in dimension to suit the preference of the user.

The term air is understood to be ambient air in the atmosphere.

For the purpose of this invention, the term extractor is understood to be any device or apparatus that draws a fluid substance in a certain direction, or is driven by a fluid substance to create mechanical movement. Examples of extractors are fans, turbines or pumps.

The term conduit is understood to be any means that conveys a fluid substance within its structure. Examples of conduits can be pipes, tubes, funnels or channels.

An inlet is understood to be any moans that allows entry of a fluid substance into the apparatus from atmosphere.

An outlet is understood to be any means that allows a fluid substance to exit into atmosphere from the apparatus.

A holder is understood to be any means or receptacle that contains or supports a substance within its structure. For example, a cup, flat plate, cylinder casing, cage or basket.

The term active substance is understood to mean any substances that provide an effect to the user's senses, such as smell, taste and touch. The active substances can be stored in sealed containment until release.

For the purpose of the invention, the active substances can be transported by air. For example, the active substance particles are fine enough to be able to be carried by ambient air and conveyed through the conduit.

In preferred embodiments exposure of the active substances to air enables the volatiles to escape without the need for vaporization or atomization. The level of volatiles escaping can be controlled by the amount of substance exposed.

In another embodiment the active substances can react with another substance to become volatile. For example, the active substances may become volatile after being in contact with another substance.

The term driving link should be understood to be any apparatus, device or means that connects the air extractor, in the said first compartment, and the active substance extractor in the said second compartment, so that when the air extractor moves, the active substance extractor will be driven by the movement, without the mixing of active substance and ambient air between the first and second compartments. For example, the driving link can be magnetic or a flexible diaphragm pump.

The term partition should be understood to be any apparatus, device or means that separates or divides any apparatus, device, or means into two separate parts.

For the purpose of the invention, the partition separates the first and second compartments of the breathing apparatus and prevents mixing of any fluid substance between the first and second compartments. Examples of the partition can include a membrane, seal, gasket, solid block and flexible diaphragm.

In operation, the device has been adapted so that the user of the breathing and aroma delivery apparatus can use the mouthpiece to generate an air flow within the first compartment.

Preferably, the user sucks the mouthpiece in order to create lower fluid pressure within the first compartment, thus in turn drawing ambient air into the first compartment, via the inward ventilation holes to flow towards the mouthpiece.

The ambient air flows through the air extractor and then out of the mouthpiece and into the user's lungs, in turn driving the air extractor to spin or move.

In a preferred embodiment the mouthpiece is a molded part of which the user can easily and comfortably apply his/her mouth to. This provides a pacifying effect to some extent.

Because the air extractor is driven by the air flow to spin or move, the driving link between the air extractor and the active substance extractor drives the active substance extractor to spin or move also.

In a preferred embodiment the air extractor is a fan with a set of blades. The angles of the blades are adjustable to achieve maximum efficiency of extraction or drive.

In a preferred embodiment the driving link is magnetic due to the ease of fluid separation between the first and second compartments.

There is provided further inward ventilation holes configured close to the active substance holder in the third compartment to allow air to be drawn into the second compartment, in order for the active substance to be carried with the air.

The inward ventilation holes also provide a visual portal for the user to monitor the condition of the active substances. For example, check if it has passed the expiry date by visual inspection.

As the active substance extractor spins or moves it draws the air containing the active substance from the holder and creates a fluid flow from the holder to the active substance outlet via a funneled conduit.

There is provided a partition that separates the first and second compartments and prevents any mixing of the fluids that are present within the respective compartments.

In a preferred embodiment the active substance is a scented sachet with therapeutic properties.

In an alternative embodiment the active substance is for medical purposes to deliver medicine (scented or unscented) to the user; such as for an asthma sufferer who would benefit from the active substance being delivered nasally.

In a preferred embodiment the active substances are configured in a shape or form to be configured to the holder of the breathing apparatus. For example, it can be a solid shape, gel, liquid, fresh or dried natural materials, or a combination of these forms in order to be able to be configured to the holder.

There are significant financial benefits to have the active substances configured such that it will be a consumable complementary product to the breathing and aroma delivery apparatus.

In a preferred embodiment the holder is a compartment with a removable cover, fastened by conventional fastening methods such as a screw-cap thread.

In a preferred embodiment at least a portion of the holder is transparent so users can monitor the condition of the active substance contained within the holder.

For the purpose of this invention, the active substance outlet is located in a position within the breathing and aroma delivery apparatus and adapted such that, when the breathing apparatus is in use by a human user, the active substance outlet is located close to the nostrils of the user.

In a preferred embodiment the active substance is introduced into the user's nostrils.

In an alternative embodiment the device is operated without an active substance, with the air flow to the nasal passages providing a gentle physical stimulus, along with improved airflow into the lungs via the mouthpiece.

For the purpose of this invention, the partition that separates the two compartments is a solid wall in between the two compartments or a fluid impervious membrane.

In one embodiment, the invention further includes a replaceable air filter configured to the conduit which connects the air extractor and the mouthpiece of the breathing apparatus in order to remove undesirable particulates.

In one embodiment, the invention further includes a replaceable air filter configured to the conduit which connects the active substance extractor and the active substance outlet of the breathing apparatus in order to filter large particles of the active substance which are not ideal to be taken in by the nostrils.

The air filters are configured within the breathing apparatus via conventional fastening mechanisms such as a detachable screw base and a molded or fitted housing or casing.

The present invention allows the user to take a long, deep and steady breath with each draw of ambient air through the invention. This expands the lungs and lifts the diaphragm more than a normal shorter breathe or a shallow breathe; as can occur when a person is experiencing tension or anxiety. While the design of the invention can be broadly associated by the user with the act of inhaling through a cigarette or drawing on a tobacco pipe, the invention can also be associated with several other calming activities, including the act of deep breathing.

Under normal aerobic conditions in the body, more air going into the user's lungs results in increased oxygen levels being absorbed through the lung capillaries, resulting in a relaxing, calming effect on the central nervous system, providing positive health benefits. The correlation between deep steady breathing and health improvements such as improved heart rate and heart rhythms; blood pressure and respiration; have been proven to exist by the Institute of Heart Math, California, USA, as referenced in their stress management system titled Freeze-Frame".

Users of the Nasal Aroma Breathing Pipe invention can potentially receive many positive benefits in terms of their physiological and psychological state, including the ability to make decisions in a more relaxed "state of mind". The said invention can also be used in conjunction with a range of known breathing techniques as applied by yoga and health practitioners, the Art of Living Foundation and organizations like the Institute of Heart Math.

In use, the said scented sachet, once opened, emits natural or human-made aromas that are combined with the air passing over the sachet. Through the Nasal Aroma Breathing Pipe the act of drawing ambient air through a chamber into the mouthpiece sends a corresponding smooth column of scented air into the user's nostrils where the major olfactory glands are located. Targeting the olfactory glands in this way removes the need to inhale scented air deeply into the lungs as occurs with other 'prior art'.

The scented sachet has preferably aroma producing substances stored in a vacuum sealed packet with one or more removable adhesive seal(s) that can be peeled-off the said packet to release the aromas. The said sachet contains oils and other fragrant materials that will remain useable for a specific time period, depending on the substances and the environment in which they are used.

The fragrant oil in each sachet can help to preserve other solid fragrant materials in the sachet and enables an improved release of their aromas, compared to dried fragrant materials on their own. The sachet packet can be gently crushed with the fingers, prior to use, to release aromas in the solid materials. The oil also plays an important role in adhering to dust particles in the sachet, minimizing the size and amount of particulates that enter the nasal passages when using the said invention.

The aromas directed for absorption in the olfactory glands are not intended by the Nasal Aroma Breathing Pipe invention to directly alter the physiology of the user, with the exception of stronger medical applications; provided low concentrations of aroma molecules in the scented air are maintained through careful sachet design and selection of fragrant materials. Instead, the intended reaction from the scented air is to provide a positive association with the user's own sense of smell and "smell memory", dependent on the aroma or combination of aromas; thereby creating positive secondary physiological and psychological benefits, whilst avoiding any significant long-term negative or cumulative health effects.

The smell association is intended to create a positive mindset and mood for the user. A wide range of scented sachets could be made available to allow the user to select their own scent preferences. The smooth flow of scented air into the user's nostrils will also provide a gentle physical stimulus that, of itself, can afford a relaxing sensation for the user, without this person having to inhale deeply through the nose.

Another calming effect, from use of the said invention, can be generated by the physical association of the mouthpiece in the mouth, similar to the act of a young child placing its thumb in its mouth for comfort. From a biological perspective this association may begin either in the womb or when a baby first suckles. This association continues into adult life and can be seen by often unconscious acts of; biting nails; fingers near or on the lips during times of increased tension; the biting of pens; and food/drink associated comfort-related consumption.

The comfort provided by the said mouthpiece can thereby be a substitute or distraction for people with negative eating and drinking habits or addictions.

The distraction can also provide a "time-out" moment for people to alter their perception of a particular situation into a more positive "state of mind".

For others using the said invention, it may be that deeper breathing or the enjoyment from mental associations with the scented aromas is what provides a greater calming effect on the health and well-being of the user. The combination of effects from the said invention can therefore offer multiple advantages for the user.

In application, the user can self-regulate the number of draws through the said invention. This advantage means the olfactory glands are less likely to be constantly saturated by the aromatic air, as can occur with air fresheners and aromatherapy devices where scents constantly surround the user in a prescribed space like a living room, reducing the ability to smell the aroma after initial contact.

DETAILED DESCRIPTION OF THE INVENTION

In two preferred embodiments the invention is configured in the shape of a tobacco pipe and smoker's cigarette. The examples detailed below show FIGS. 1 and 2 as a Bowl Pipe and FIGS. 3 and 4 as a Cylinder Pipe.

Embodiment 1

Bowl Pipe

With reference to FIG. 1 and FIG. 2, the bowl pipe configuration includes; a bowl (1), a stem (2) and mouthpiece (7). An internal cylinder (8) inside the bowl, houses a dual fan mechanism comprising air extractor blades (9) and active substance extractor blades (10) which consist of fan blades extending away from central axles (11) and (12) in a perpendicular direction; the axles are connected to magnets (13) and (14). The said blades can be tilted to provide the appropriate level of air resistance when air is drawn through the inward air channel (3) which causes air extractor blades (9) and axle (11) to spin in Compartment (A), and in tandem, axle (12) and fan blades (10) turn to generate a resulting level of air propulsion in Compartment (B) directing air to the user's nostrils via external air channel (4) and outlet nozzle (5).

Ambient air is drawn through mouthpiece (7) and into the user's lungs and within funnel 20 or external air channel (6) it is possible to include a replaceable air fitter (made of a reasonably dense but still penetrable substance) with the potential to remove some large air pollution or naturally occurring particulates.

In order for air to reach the mouthpiece the air has traveled from inward ventilation holes (3), into compartment (A), then through air extractor blades (9) and into funnel (20), the air is then drawn into external air channel (6); when this airflow contacts the internal blades (9) in compartment (A) they spin, turning axle (11) and magnet (13). Magnets (13) and (14) have a magnetic connection across an impervious membrane (15), ensuring fan blades (9) and (10) and axles (11) and (12) move simultaneously without air mixing across the said compartments. Magnet (13) sits on the upstream end of axle (11).

At the top of the bowl is a removable cover (16) with screw-cap thread (17). Under the removable cover is a third compartment (18) for housing an active substance (19). An inward flow of ambient air molecules is drawn into compartment (18) via inward ventilating holes (22), this activity allows aromas from the said active substance to be combined with the said ambient air; these holes may also indicate when the active substance expiry date is reached, through an oxidation process that over a prescribed time changes color to indicate when the active substance replacement is necessary.

When active substance extractor blades (10) turn in response to the movement of air extractor blades (9), it creates a partial vacuum drawing ambient air down through inward ventilation holes (22) and the third compartment (18). The active substance is then drawn through permeable gauze membrane (23) into compartment (B) until it is propelled by (10) and then funneled by (21) into external air channel (4), exiting the unit via an outlet nozzle (5). The base of the funnel (21) contains a roller bearing (21B) through which axle (12) can turn. Magnet (14) sits below roller bearing (21B) on the end of axle (12).

When the active substance is expelled out of outlet nozzle (5) it is concentrated into a thin column of air and directed by this nozzle into the user's nostrils. A detachable directional component (acting as an air channel extension) may be attached to the nozzle to alter the angle at which air is directed into the nose.

Embodiment 2

Cylinder Pipe

With reference to FIGS. 3 and 4, this type of Cylinder Pipe configuration includes; a cylinder (25), a mouthpiece (30) and removable cover (45). Inside cylinder (25) are three compartments (C), (D) and (39) housing dual fan mechanisms (31) an air extractor and (32) an active substance extractor, with blades extending away from central axles (33) and (34) in a perpendicular direction; the axles are connected to magnets (35) and (36). The said blades can be tilted to provide the appropriate level of air resistance and resulting axle spin in compartment (C), and in tandem the appropriate level of air propulsion in compartment (D) directing air into the user's nostrils.

Ambient air is drawn through mouthpiece (30) and into the user's lungs and within the said mouthpiece it is possible to include a replaceable air filter (made of a reasonably dense but still penetrable substance) with the potential to remove some large air pollution or naturally occurring particulates. Access to the replaceable filter would be via a detachable mouthpiece (30) with screw thread attaching to the cylinder (25).

In order for air to reach the mouthpiece, the air has traveled from one or more inward ventilation holes (26) into compartment (C), through air extractor blades (31) and into funnel (29); when this airflow contacts the air extractor blades (31) in compartment (C) they spin, turning axle (33) and magnet (35). Magnets (35) and (36) have a magnetic connection across an impervious membrane (37), ensuring the air extractor blades (31) and active substance extractor blades (32) move simultaneously without air mixing between compartments (C) and (D).

At the opposite end to the mouthpiece (30) of cylinder (25) there is a removable cylinder cover (45) with inward ventilation holes (42) and screw cap thread (38). Inside cylinder cover (45) there is a third compartment (39) to house an active substance (40). The end of cylinder cover (45) may be transparent to identify the expiry date or time, of the active substance.

Ambient air is drawn through inward ventilation holes (42) and then passes into compartment (39) and over the active substance (40), then through a permeable gauze membrane (43) and into chamber (D).

Within the cylinder cover (45) and third compartment (39) there is a perforated inner casing (46) for housing the active substance (40). The said perforated inner casing holds the active substance in place and allows aromas from the said active substance to be easily combined with air molecules entering via the inward ventilation holes (42).

When active substance extractor blades (32) turn in response to the movement of air extractor blades (31), it creates a partial vacuum drawing ambient air down through inward ventilation holes (42) and the third compartment (39). The active substance is then drawn through permeable gauze membrane (43) and into compartment (D), until it is propelled by (32) and then funneled by (41) into external air channel (27), exiting the unit via an outlet nozzle (28). The base of the funnel (41) contains a roller bearing (41D) through which axle (34) can turn. Magnet (36) is located to the right of (41D) on the end of axle (34).

When the active substance is expelled out of external air channel (27) and outlet nozzle (28), it is concentrated into a thin column of air that is directed by the nozzle into the user's nostrils. A detachable directional component may be attached to the nozzle to after the angle at which air is directed into the user's nose.

Aspects of the present invention have been described by way of example only and it should be appreciated that modifications and additions may be made thereto without departing from the scope thereof as defined in the appended claims.

SEQUENCE LISTING

Not Applicable.

I claim:

1. A breathing and aroma delivery apparatus comprising:

a first compartment, a second compartment, and a third compartment;

a mouthpiece, said mouthpiece being attached to the first compartment and forming an air outlet adapted for allowing a user to draw air through an end of the mouthpiece; and a driving link located between the first and second compartments, the driving link creating a mechanical coupling between the first and second compartments;

wherein the driving link is separated by a partition that prevents mixing of gases between the first and second compartments;

wherein said first compartment comprises:

an air extractor, said air extractor comprising a center axle with fan blades that extend in a perpendicular direction from the center axle, the center axle extending in a longitudinal direction within the first compartment;

a funnel and an external air channel, said funnel and said external air channel concentrating ambient air when propelled from the air extractor through the mouthpiece and the air outlet; and one or more air inward ventilation holes located upstream of the air extractor and in communication with atmosphere;

wherein said second compartment comprises:

an active substance extractor, said active substance extractor extracting an active substance transported by air, said active substance extractor comprising a center axle with fan blades extending in a perpendicular direction from the center axle, the center axle extending in a longitudinal direction within the second compartment;

a funnel, an external air channel, and an outlet nozzle, said funnel, said external air channel, and said outlet nozzle concentrating and propelling the active substance from the active substance extractor to outside of the device, the outlet nozzle being adapted to direct the active substance into a user's nostrils;

wherein said third compartment comprises:

a holder for holding the active substance, the active substance capable of being transported by air and becoming volatile when exposed to the atmosphere; inward ventilating holes, said inward ventilating holes being upstream of the active substance and connecting the third compartment with the atmosphere to allow air to be drawn into the third compartment and over the active substance; and a permeable membrane, said membrane allowing the active substance to be drawn from the third compartment and into the second compartment; and wherein when the user inhales through the mouthpiece, the air extractor rotates, causing the active substance extractor to rotate via the driving link, which propels active substance into the user's nostrils while the user inhales ambient air through the air outlet of the mouthpiece.

2. A breathing and aroma delivery apparatus as claimed in claim 1, wherein the said driving link is magnetic.

* * * * *